United States Patent [19]

Hunter et al.

[11] 4,177,057

[45] Dec. 4, 1979

[54] HERBICIDAL BENZIMIDAZOLES

[75] Inventors: Don L. Hunter, Anaheim, Calif.; Wayne S. Belles, Moscow, Id.

[73] Assignee: United States Borax & Chemical Corporation, Los Angeles, Calif.

[21] Appl. No.: 916,669

[22] Filed: Jun. 19, 1978

Related U.S. Application Data

[63] Continuation-in-part of Ser. No. 844,777, Oct. 25, 1977, abandoned.

[51] Int. Cl.² ............................................. A01N 9/22
[52] U.S. Cl. ..................................................... 71/92
[58] Field of Search ............................. 71/92; 548/325

[56] References Cited

U.S. PATENT DOCUMENTS

| | | | |
|---|---|---|---|
| 3,325,271 | 6/1967 | Goldsmith et al. | 71/92 X |
| 3,412,101 | 11/1968 | Zwahlen | 71/92 X |
| 3,890,344 | 1/1975 | Horlein et al. | 71/92 X |
| 3,901,910 | 8/1975 | Hunter et al. | 71/92 X |
| 3,954,438 | 5/1976 | Hunter et al. | 71/92 |

OTHER PUBLICATIONS

Sedova et al. Chem. Abst., vol. 72, (1970), 31366g.

*Primary Examiner*—Catherine L. Mills
*Attorney, Agent, or Firm*—James R. Thornton

[57] ABSTRACT

1,2-Di-lower alkyl-5-lower alkylsulfonylbenzimidazoles useful as selective herbicides. In the preferred compounds, the 5-substituent is a fluorinated lower alkyl sulfonyl group.

13 Claims, No Drawings

HERBICIDAL BENZIMIDAZOLES

This is a continuation-in-part of our co-pending application Ser. No. 844,777 filed Oct. 25, 1977, now abandoned.

This invention relates to a class of herbicidal benzimidazoles which are especially useful as selective herbicides.

BACKGROUND OF THE INVENTION

Various substituted benzimidazoles are known to be useful as herbicides. U.S. Pat. No. 3,325,271 describes the use as herbicides of a broad class of substituted benzimidazoles in which there is at least one substituent on the aromatic ring or at the 1- or 2-position of the molecule. The aromatic substituents may be selected from nitro, halo, lower alkyl, lower alkoxy and halo lower alkyl. U.S. Pat. No. 3,412,101 describes a specific group of 2-trifluoromethyl-5-alkylsulfonylbenzimidazoles which have herbicidal activity. U.S. Pat. No. 3,890,344 describes a class of herbicidal 2-haloalkyl-haloalkylsulfonylbenzimidazoles having no 1-substituent. Other patents relating to benzimidazoles are U.S. Pat. Nos. 3,954,438; 3,901,910; 3,652,580; 3,472,865; 3,480,643; 3,531,495; 3,721,678; 3,821,393 and 3,430,259. Some of the compounds employed in the present herbicidal method are known compounds. See, for example, Bannert et al., *Chem. Abstracts*, Vol. 78, 99066; Sedova et al., *Chem. Abstracts*, Vol. 72, 31366; Troitskaya et al., *Chem. Abstracts*, Vol. 79, 54858 and Yagupol'skii et al., *Chem. Abstracts*, Vol. 53, 21765–21766.

SUMMARY OF THE INVENTION

This invention relates to a class of selective herbicidal benzimidazoles having lower alkyl substituents at both the 1- and 2-positions and a lower alkylsulfonyl group at the 5-position of the molecule. We have found that this group of benzimidazoles possesses superior herbicidal properties, both as pre- and post-emergence applications and that they are especially useful as selective herbicides in desirable crops since they possess unexpected crop tolerance.

According to the present invention, there are provided herbicidal compositions and methods utilizing benzimidazole compounds of the formula:

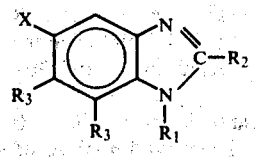

in which each of $R_1$ and $R_2$ are lower alkyl of one to about three carbon atoms, X represents a lower alkylsulfonyl or fluoro-lower alkylsulfonyl group and each of said $R_3$'s is selected from hydrogen, halo, lower alkoxy, nitro and amino groups. Thus the 1-, 2- and 5-substituents represented by $R_1$, $R_2$ and X, respectively, in the above formula, are essential. Optionally, the benzimidazole molecule may contain other substituents at the 6- and 7-positions such as can be represented by $R_3$. Examples of such optional substituents include chloro, bromo, fluoro, methoxy, and ethoxy, as well as the nitro and amino groups. Preferably, both $R_3$'s are hydrogen. The $R_1$ and $R_2$ groups are lower alkyl such as methyl, ethyl, n-propyl and isopropyl. Examples of the lower alkylsulfonyl groups and fluorinated derivatives thereof which may be represented by X include methylsulfonyl, ethylsulfonyl, propylsulfonyl, and isopropylsulfonyl, as well as the mono-, di-, tri- and perfluorinated derivatives thereof. In a preferred embodiment of the invention, X represents fluoro-lower alkylsulfonyl, especially difluoromethylsulfonyl and trifluoromethylsulfonyl.

The compounds of this invention are readily prepared by several procedures such as by reaction of the corresponding ortho-phenylenediamine with an alkanecarboxylic acid ($R_2COOH$), the anhydride or halide thereof, or a carboximidate

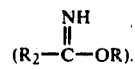

The various intermediates are prepared by synthetic procedures well-known to the organic chemical art. A typical synthetic procedure is illustrated below in which $R_1$, $R_2$ and X have the significance previously assigned, and R is a lower alkyl group.

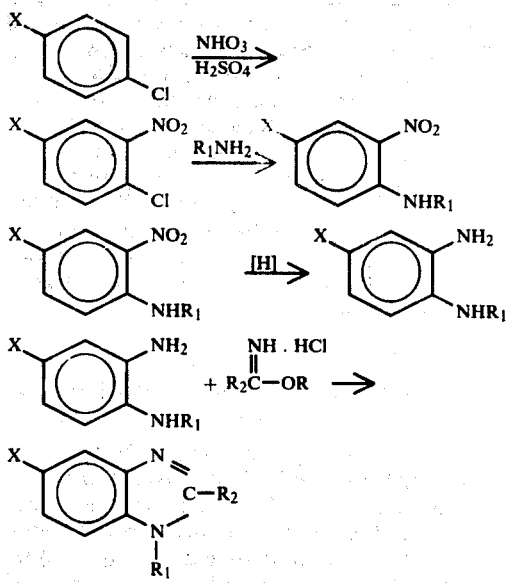

When the benzimidazole-forming reaction employs a carboximidate, it is generally in its hydrochloride salt form. When an alkanecarboxylic acid is used to form the benzimidazole, the reaction takes place in the presence of a mineral acid. Optional substituents represented by $R_3$ can be added to the molecule by conventional procedures, generally prior to the benzimidazole-forming step. The desired products are isolated from the reaction mixtures and purified by conventional procedures.

The following examples illustrate the preparation of representative compounds of this invention.

EXAMPLE 1

1-ethyl-2-methyl-5-methylsulfonylbenzimidazole

To 5.06 g. (23.6 mmoles) of $N^1$-ethyl 4-methylsulfonyl-1,2-phenylenediamine was added 5.84 g. (47.2 mmoles; 100% excess) of ethyl methylcarboximidate hydrochloride and 75 ml. of anhydrous ethanol. The mixture was stirred for 6 hours at room temperature and then for 17.5 hours at reflux temperature. The solvent was removed by distillation under reduced pressure, 100 ml. of 4 N HCl was added, and the resultant mixture heated at reflux temperature for 7 hours. After cooling, the mixture was filtered and the filtrate poured into a mixture of 400 ml. of ice water +60 ml. of conc. ammonium hydroxide. The resultant mixture was extracted thrice with 100 ml. portions of chloroform and the combined chloroform extracts dried over anhydrous sodium sulfate. Removal of the solvent by distillation under reduced pressure gave 3.61 g. (64%) of the desired benzimidazole, melting at 140°–142° C.

EXAMPLE 2

1-ethyl-2-methyl-5-difluoromethylsulfonylbenzimidazole $N^1$-Ethyl 4-difluoromethyl-1,2-phenylenediamine (4.17 g.; 16.7 mmoles) dissolved in 50 ml. of dimethoxyethane was heated to reflux temperature. To the stirred, heated solution was added, dropwise, 1.87 g. (18.3 mmoles; 10% excess) of acetic anhydride over a period of 10 minutes. The mixture was refluxed for 4 hours and then 5 ml. of concentrated hydrochloric acid was added, dropwise, over 15 minutes. After refluxing an additional 18 hours, the solvent was removed by distillation under reduced pressure and the resultant residue dissolved in chloroform. The chloroform solution was washed with a mixture of 20 ml. of ammonium hydroxide plus 100 ml. of water and then again with 100 ml. of water. After drying over anhydrous sodium sulfate, the chloroform solution was evaporated to dryness to give 4.45 g. of residue which was dissolved in 100 ml. of hot carbon tetrachloride. The product crystallized from the $CCl_4$ upon cooling and was recrystallized from benzene to give 3.18 g. (70%) of the desired benzimidazole, melting at 160°–161.5° C.

EXAMPLE 3

1-isopropyl-2-methyl-5-methylsulfonyl-6-methoxybenzimidazole

A solution of 5.08 g. (0.020 mole) of $N^1$-isopropyl 5-methoxy-4-methylsulfonyl-1,2-phenylenediamine, 4.86 g. (0.040 mole) of ethyl methylcarboximidate hydrochloride and 75 ml. of absolute ethanol was stirred at room temperature for four hours and then refluxed for 16 hours. The solvent was removed by distillation under reduced pressure and the residue dissolved in 100 ml. of 4 N HCl and refluxed for 21 hours. The reaction mixture was then cooled to room temperature, filtered and the filtrate added, dropwise, to 300 ml. of a stirred mixture of ice containing 75 ml. of concentrated ammonium hydroxide. The aqueous mixture was then extracted thrice with 100 ml. of chloroform. The combined chloroform extracts were dried over anhydrous sodium sulfate, filtered and then the filtrate evaporated to dryness under reduced pressure to give the desired product (5.14 g.; 92.6%) melting at 161°–165° C.

EXAMPLE 4

1-ethyl-2-methyl-5-methylsulfonyl-6-chloro-7-nitrobenzimidazole

To a stirred, cooled solution of 40 ml. of concentrated sulfuric acid (at 0°–5° C.) was added, dropwise, 4.0 g. (0.015 mole) of 1-ethyl-2-methyl-5-methylsulfonyl-6-chlorobenzimidazole. Stirring was continued until all solid was in solution. To this stirred and cooled solution was added 6.0 g. (0.086 mole) of 90% fuming nitric acid, dropwise, over a 30 minute period. Stirring was continued while cooling for 9 hours and then the reaction mixture allowed to warm to room temperature over a 14 hour period. An additional 13.5 g. of 30% fuming sulfuric acid was then added, dropwise. The reaction mixture was stirred for about 24 hours and then stirred at about 40° C. for an additional 64 hours. The resultant reaction mixture was poured into a stirred mixture of 300 ml. of ice +200 ml. of concentrated ammonium hydroxide. The resultant aqueous mixture was extracted thrice with 100 ml. portions of chloroform and the combined chloroform extracts dried over anhydrous sodium sulfate. The resultant chloroform solution was evaporated to dryness under reduced pressure to give 3.04 g. (73.4%) of the desired product, melting at 75°–79° C.

EXAMPLE 5

1-ethyl-2-methyl-5-methylsulfonyl-6-chloro-7-aminobenzimidazole

1-Ethyl-2-methyl-5-methylsulfonyl-6-chloro-7-nitrobenzimidazole (2.50 g.) was combined with 75 ml. of methanol and 0.2 g. of 87% platinum oxide catalyst in a hydrogenation bottle. The bottle was charged with 37 psi of hydrogen and shaken at room temperature for 22.5 hours. The resultant reaction mixture was filtered to remove the catalyst and the filtrate evaporated to dryness under reduced pressure to give 2.27 g. (100%) of the desired 7-amino derivative, melting at 179°–186° C.

Examples of other compounds embraced by the present invention which may be prepared by the above described procedures include the following:

EXAMPLES 6–42

6. 1-isopropyl-2-methyl-5-methylsulfonyl-7-aminobenzimidazole, m. p. 161°–163° C.
7. 1-isopropyl-2-methyl-5-methylsulfonylbenzimidazole, m. p. 143°–147° C.
8. 1,2-dimethyl-5-difluoromethylsulfonylbenzimidazole, m. p. 171°–172° C.
9. 1,2-dimethyl-5-methylsulfonylbenzimidazole, m. p. 158.5°–160° C.
10. 1,2-dimethyl-5-methylsulfonyl-6-chloro-7-aminobenzimidazole, m. p. 230°–234° C.
11. 1-isopropyl-2-methyl-5-methylsulfonyl-6-chloro-7-aminobenzimidazole, m. p. 165°–178° C.
12. 1,2-dimethyl-5-methylsulfonyl-6-methoxy-7-aminobenzimidazole, m. p. 201°–204° C.
13. 1-ethyl-2-methyl-5-methylsulfonyl-6-methoxy-7-aminobenzimidazole, m. p. 164°–170° C.
14. 1-isopropyl-2-methyl-5-methylsulfonyl-6-methoxy-7-aminobenzimidazole, m. p. 90°–98° C.
15. 1,2-dimethyl-5-methylsulfonyl-6-chloro-7-nitrobenzimidazole, m. p. 220°–223° C.
16. 1-isopropyl-2-methyl-5-methylsulfonyl-6-chloro-7-nitrobenzimidazole, m. p. 82°–86° C.
17. 1,2-dimethyl-5-methylsulfonyl-6-methoxy-7-nitrobenzimidazole, m. p. 168°–170° C.
18. 1-ethyl-2-methyl-5-methylsulfonyl-6-methoxy-7-nitrobenzimidazole, glass
19. 1-isopropyl-2-methyl-5-methylsulfonyl-6-methoxy-7-nitrobenzimidazole, m. p. 60°–70° C.
20. 1,2-dimethyl-5-methylsulfonyl-6-chlorobenzimidazole, m. p. 70°–80° C.
21. 1-ethyl-2-methyl-5-methylsulfonyl-6-chlorobenzimidazole, m. p. 65°–75° C.

22. 1-isopropyl-2-methyl-5-methylsulfonyl-6-chlorobenzimidazole, m. p. 95°–115° C.
23. 1,2-dimethyl-5-methylsulfonyl-6-methoxybenzimidazole, m. p. 195°–198° C.
24. 1-ethyl-2-methyl-5-methylsulfonyl-6-methoxybenzimidazole, m. p. 188°–191° C.
25. 1,2-dimethyl-5-trifluoromethylsulfonylbenzimidazole, m. p. 158°–159° C.
26. 1-ethyl-2-methyl-5-trifluoromethylsulfonylbenzimidazole, m. p. 163°–164° C.
27. 1,2-dimethyl-5-isopropylsulfonylbenzimidazole, m. p. 155.5°–157° C.
28. 1,2-dimethyl-5-difluoromethylsulfonyl-6-nitrobenzimidazole, m. p. 140°–142° C.
29. 1-ethyl-2-methyl-5-perfluoroethylsulfonylbenzimidazole
30. 1-isopropyl-2-methyl-5-difluoromethylsulfonyl-7-aminobenzimidazole, m. p. 218°–221° C.
31. 1-methyl-2-propyl-5-methylsulfonylbenzimidazole
32. 1-isopropyl-2-methyl-5-difluoromethylsulfonyl-6-chlorobenzimidazole, m. p. 124.5°–125.5° C.
33. 1,2-diethyl-5-fluoromethylsulfonylbenzimidazole
34. 1-methyl-2-ethyl-5-ethylsulfonyl-6-chlorobenzimidazole
35. 1-n-propyl-2-methyl-5-difluoromethylsulfonyl-6-bromobenzimidazole
36. 1,2-dimethyl-5-methylsulfonyl-6-fluorobenzimidazole
37. 1-methyl-2-ethyl-5-difluoromethylsulfonyl-6-methoxybenzimidazole
38. 1-isopropyl-2-methyl-5-trifluoromethylsulfonylbenzimidazole, m. p. 128°–130° C.
39. 1-ethyl-2-methyl-5-isopropylsulfonylbenzimidazole
40. 1-isopropyl-2-methyl-5-difluoromethylsulfonylbenzimidazole, m. p. 120.5°–123° C.
41. 1-methyl-2-ethyl-5-difluoromethylsulfonyl-7-nitrobenzimidazole
42. 1-ethyl-2-methyl-5-difluoromethylsulfonyl-7-aminobenzimidazole The compounds of this invention are useful as selective herbicides for controlling weeds in crops. They can be applied as either a pre-emergence or a post-emergence treatment; that is, they can be applied to soil in which the weeds will grow to kill or suppress the emergence of seedlings of undesirable plants or they can be applied to the foliage of the young, growing plants after emergence from the soil. Thus, the compounds can be used to control the growth of weeds by applying a phytotoxic amount of one or more of the active compounds of this invention to the locus to be protected; that is, soil in which the weeds are growing or will grow or the foliage of the growing plants. When used as a pre-emergence treatment, the compounds may be applied to the soil surface prior to emergence of the weeds or, preferably, are incorporated, such as by mixing into the top 1 to 3 inches (2.5 to 8 cm.) of the soil prior to planting the crop. When used as a post-emergence treatment, it is preferred that a directed spray be employed, thereby directing the application of the herbicide onto the foliage of the weeds and away from the foliage of the desirable crop plants. Weeds, as used herein, is meant to include any plant growth which is undesirable.

The compounds are especially useful for selectively controlling weeds in the presence of desirable crops such as peanuts, corn, rice, wheat and, when applied pre-emergence with incorporation, soybeans, peanuts and cotton. The weeds controlled include many of the broadleaf and grassy weeds such as lambsquarter, mustard, pigweed, sesbania, velvetleaf, cocklebur, prickly sida, ragweed, jimsonweed, and morningglory.

The compounds having a fluorinated lower alkylsulfonyl group at the 5-position of the molecule provide superior selective weed control, especially on the broadleaf weed species such as pigweed, sesbania, prickly sida and morningglory. Such compounds represent a preferred embodiment of this invention.

Generally, an application rate of from about 0.25 to about 10 pounds (about 0.1 to 5 kg.) of one or more of the active compounds per acre is effective in controlling weed growth. Preferably, an application rate in the range of about 0.5 to 5 pounds (about 0.2 to 2.5 kg.) per acre is employed.

The following examples illustrate the herbicidal activity of representative compounds of this invention.

EXAMPLE 43

The compounds to be tested were evaluated as both a pre-emergence and post-emergence treatment. Greenhouse flats were planted to soybeans (SB), velvetleaf (VL), oats (O) and millet (M). The flats were sprayed on the same day as planting with an ethanol solution (sometimes containing added dioxane) of the compound to be tested at a rate of 5 pounds (2.3 kg.) per acre. Another set of flats with the same plants was treated after the plants had emerged and were about one inch (2.5 cm.) in height. These flats were also sprayed with the solution of the compound to be tested at a rate of 5 pounds (2.3 kg.) per acre. The flats were kept in the greenhouse and watered when needed. Twenty-one days after treatment, the flats were examined and the plants rated for herbicidal activity on a 0–9 scale in which 0 = no effect
1 = <10% injury
2 = 10–40% injury
3 = 40–70% injury
4 = >70% injury
5 = <25% kill
6 = 25–50% kill
7 = 50–75% kill
8 = 75–99% kill
9 = 100% kill The results are given in Table I.

TABLE I

| | Activity | | | | | | | |
|---|---|---|---|---|---|---|---|---|
| | Pre | | | | Post | | | |
| Compd. No. | SB | VL | O | M | SB | VL | O | M |
| 1 | 3 | 7 | 1 | 5 | 6 | 9 | 1 | 2 |
| 2 | 8 | 9 | 9 | 9 | 9 | 9 | 9 | 9 |
| 3 | 3 | 9 | 1 | 0 | 4 | 9 | 0 | 0 |
| 4 | 0 | 0 | 0 | 0 | 0 | 9 | 0 | 0 |
| 5 | 0 | 5 | 0 | 0 | 7 | 9 | 0 | 0 |
| 6 | 0 | 0 | 0 | 0 | 2 | 8 | 0 | 1 |
| 7 | 6 | 5 | 2 | 5 | 4 | 9 | 5 | 0 |
| 8 | 6 | 9 | 8 | 8 | 9 | 9 | 9 | 7 |
| 9 | 3 | 5 | 0 | 0 | 4 | 9 | 1 | 1 |
| 10 | 1 | 0 | 0 | 0 | 2 | 9 | 0 | 0 |
| 11 | 1 | 9 | 0 | 0 | 9 | 9 | 0 | 0 |
| 12 | 0 | 0 | 0 | 0 | 1 | 9 | 0 | 0 |
| 13 | 0 | 0 | 0 | 0 | 5 | 9 | 0 | 0 |
| 14 | 0 | 0 | 0 | 0 | 3 | 9 | 0 | 0 |
| 15 | 0 | 0 | 0 | 0 | 0 | 9 | 0 | 0 |
| 16 | 0 | 0 | 0 | 0 | 0 | 9 | 0 | 0 |
| 17 | 0 | 0 | 0 | 0 | 2 | 7 | 0 | 0 |
| 18 | 1 | 0 | 0 | 0 | 3 | 8 | 0 | 0 |
| 19 | 0 | 0 | 0 | 0 | 1 | 9 | 6 | 0 |
| 20 | 2 | 9 | 0 | 0 | 3 | 9 | 0 | 0 |
| 21 | 3 | 9 | 1 | 2 | 9 | 9 | 5 | 6 |

TABLE I-continued

| | Activity | |
|---|---|---|
| | Pre | Post | an average of two replicates. Where two numbers are used, i.e., 8/4, the first number represents the percent kill and the second number is the injury to the remaining plants.

TABLE II

| | | Activity - Post | | | | | | | |
|---|---|---|---|---|---|---|---|---|---|
| Plant | Rate | Compd. 3 | | Compd. 4 | | Compd. 5 | | Compd. 9 | |
| Species | (lb./A) | 1 | 2 | 1 | 2 | 1 | 2 | 1 | 2 |
| alfalfa | | 5/2 | 7/3 | 0 | 5/2 | 8/3 | 8/4 | 9 | 9 |
| corn | | 0 | 0 | 0 | 0 | 0 | 0 | 0 | 0 |
| cotton | | 0 | 1 | 0 | 0 | 8/3 | 9 | 8/3 | 6/3 |
| dry beans | | 4 | 5/4 | 3 | 7/4 | 8/3 | 9 | 7/4 | 7/4 |
| peanuts | | 1 | 2 | 0 | 0 | 0 | 0 | 0 | 2 |
| rice | | 0 | 0 | 0 | 0 | 0 | 0 | 0 | 0 |
| soybeans | | 2 | 3 | 0/1 | 0/2 | 1 | 3 | 3 | 5/4 |
| wheat | | 0 | 0 | 0 | 0 | 0 | 0 | 0 | 0 |
| cocklebur | | 5/2 | 7/3 | 7/4 | 7/4 | 9 | 9 | 9 | 9 |
| jimsonweed | | 6/2 | 6/3 | 5/2 | 8/4 | 8/3 | 8/4 | 8/3 | 9 |
| lambsquarters | | 5/2 | 7/3 | 6/2 | 8/3 | 7/4 | 8/4 | 8/4 | 8/4 |
| morningglory | | 4 | 5/3 | 0 | 2 | 3 | 6/3 | 4 | 5/4 |
| mustard | | 7/3 | 8/3 | 8/2 | 8/4 | 9 | 9 | 9 | 9 |
| prickly sida | | 2 | 5/2 | 5/2 | 7/3 | 0 | 2 | 6/4 | 8/4 |
| pigweed | | 2 | 7/3 | 8/3 | 8/4 | 8/3 | 8/4 | 8/3 | 8/4 |
| sesbania | | 5/1 | 3 | 7/3 | 8/4 | 7/2 | 8/3 | 3 | 5/3 |
| velvetleaf | | 8/1 | 8/3 | 8/2 | 9 | 9 | 9 | 8/4 | 9 |
| barnyardgrass | | 0 | 0 | 0 | 0 | 0 | 0 | 0 | 0 |
| foxtail | | 0 | 0 | 0 | 2 | 0 | 0 | 0 | 0 |
| Johnsongrass | | 0 | 0 | 0 | 0 | 0 | 0 | 0 | 0 |
| wild oats | | 0 | 0 | 0 | 0 | 0 | 0 | 0 | 0 |

| | | Activity - Post | | | | | | | |
|---|---|---|---|---|---|---|---|---|---|
| Plant | Rate | Compd. 13 | | Compd. 21 | | Compd. 2 | | Compd. 8 | |
| Species | (lb./A) | 1 | 2 | 1 | 2 | 1 | 2 | 1 | 2 |
| alfalfa | | 5/2 | 8/4 | 7/3 | 8/3 | 7/1 | 9 | 9 | 9 |
| corn | | 0 | 0 | 0 | 0 | 0 | 0/1 | 0 | 0 |
| cotton | | 2 | 9 | 5/3 | 5/4 | 9 | 9 | 6/3 | 5/3 |
| dry beans | | 0/4 | 7/4 | 2 | 4 | 7/2 | 8/4 | 7/3 | 8/3 |
| peanuts | | 0 | 0 | 0 | 0 | 0/1 | 0/1 | 0 | 0/1 |
| rice | | 0 | 0 | 0 | 0 | 6/3 | 8/4 | 5/2 | 6/3 |
| soybeans | | 0 | 3 | 2 | 3 | 0/2 | 6/3 | 0/2 | 0/3 |
| wheat | | 0 | 0 | 0 | 0 | 5/2 | 7/4 | 0/1 | 5/3 |
| cocklebur | | 8/4 | 9 | 8/3 | 8/4 | 9 | 9 | 9 | 9 |
| jimsonweed | | 9 | 8/2 | 5/4 | 9 | 8/4 | 9 | 9 | 9 |
| lambsquarters | | 5/2 | 9 | 9 | 9 | 8/3 | 9 | 8/4 | 7/3 |
| morningglory | | 9 | 9 | 6/3 | 7/4 | 9 | 9 | 8/1 | 7/4 |
| mustard | | 7/2 | 9 | 9 | 9 | 8/4 | 8/4 | 9 | 8/4 |
| prickly sida | | 2 | 6/2 | 5/3 | 7/3 | 9 | 9 | 6/2 | 8/3 |
| pigweed | | 7/3 | 8/3 | 9 | 9 | 5/2 | 8/1 | 6/1 | 6/1 |
| sesbania | | 7/3 | 9 | 9 | 9 | 7/3 | 8/3 | 7/3 | 7/4 |
| velvetleaf | | 6/3 | 9 | 9 | 9 | 9 | 9 | 8/2 | 8/1 |
| barnyardgrass | | 0 | 0 | 0 | 0 | 5/2 | 5/3 | 0 | 5/1 |
| foxtail | | 0 | 0 | 0 | 0 | 5/1 | 6/2 | 0 | 0 |
| Johnsongrass | | 0 | 0 | 0 | 0 | 0 | 1 | 0 | 0 |
| wild oats | | 0 | 0 | 0 | 0 | 5/1 | 8/2 | 0 | 7/3 |
| ragweed | | — | — | — | — | 7/2 | 8/1 | 0/1 | 6/2 |
| nightshade | | — | — | — | — | 9 | 9 | 6/3 | 8/3 |

| Compd. No. | SB | VL | O | M | SB | VL | O | M |
|---|---|---|---|---|---|---|---|---|
| 22 | 4 | 9 | 1 | 0 | 4 | 9 | 2 | 0 |
| 23 | 0 | 0 | 0 | 0 | 1 | 8 | 0 | 0 |
| 24 | 1 | 1 | 0 | 0 | 2 | 9 | 0 | 0 |
| 25 | 4 | 9 | 5 | 8 | 8 | 9 | 6 | 9 |
| 26 | 9 | 9 | 5 | 9 | 8 | 9 | 7 | 8 |
| 27 | 5 | 9 | 2 | 6 | 4 | 9 | 5 | 8 |
| 28 | 0 | 5 | 0 | 0 | 2 | 9 | 5 | 6 |
| 30 | 0 | 8 | 5 | 1 | 1 | 9 | 5 | 0 |

EXAMPLE 44

Several compounds were evaluated as post-emergence herbicides in greenhouse tests with a broad group of crops and weeds. The compounds were applied as an ethanol solution at rates of 1 and 2 pounds (0.45 and 0.9 kg.) per acre to the plants when they were about one inch (2.5 cm.) in height. Twenty-one days after treatment, the plants were rated on the 0 to 9 scale described in Example 43. The results are given in Table II and are

EXAMPLE 45

Compounds 2 and 8 were also evaluated as pre-emergence herbicides against the same broad group of crops and weeds at 1 and 2 pounds (0.45 and 0.9 kg.) per acre. The greenhouse flats were planted and then on the same day sprayed with an ethanol solution of the compound. Evaluations were made twenty-one days after treatment as described in Example 44. The results are given in Table III.

TABLE III

| | Activity - Pre | | | |
|---|---|---|---|---|
| Plant | Compd. 2 (lb./A.) | | Compd. 8 (lb./A.) | |
| Species | 1 | 2 | 1 | 2 |
| alfalfa | 9 | 9 | 9 | 9 |
| corn | 0/1 | 0/1 | 0/1 | 0/1 |
| cotton | 7/3 | 9 | 5/3 | 9 |

TABLE III-continued

| Plant | Activity - Pre | | | |
|---|---|---|---|---|
| | Compd. 2 (lb./A.) | | Compd. 8 (lb./A.) | |
| Species | 1 | 2 | 1 | 2 |
| dry beans | 7/2 | 9 | 9 | 9 |
| peanuts | 0 | 0/1 | 0 | 0 |
| rice | 5/3 | 8/3 | 5/2 | 7/3 |
| soybeans | 0/1 | 0/3 | 0/1 | 5/3 |
| wheat | 6/2 | 9 | 0/2 | 5/3 |
| cocklebur | 9 | 9 | 8/3 | 8/3 |
| jimsonweed | 8/3 | 8/4 | 8/4 | 8/4 |
| lambsquarters | 8/4 | 9 | 9 | 9 |
| morningglory | 8/4 | 9 | 8/3 | 9 |
| mustard | 9 | 9 | 9 | 8/4 |
| prickly sida | 9 | 9 | 7/3 | 9 |
| pigweed | 8/2 | 8/4 | 9 | 9 |
| sesbania | 9 | 9 | 8/3 | 9 |
| velvetleaf | 9 | 9 | 8/4 | 8/4 |
| barnyardgrass | 5/2 | 9 | 5/2 | 5/2 |
| foxtail | 6/2 | 8/4 | 2 | 7/2 |
| Johnsongrass | 0/1 | 5/3 | 1 | 1 |
| wild oats | 6/1 | 9 | 6/2 | 8/3 |
| ragweed | 8/3 | 9 | 8/2 | 9 |
| nightshade | 7/3 | 7/4 | 8/4 | 7/3 |

EXAMPLE 46

Compounds 1, 2 and 8 were tested at 0.5 and 1 pound (0.2 and 0.4 kg.) per acre as a pre-emergence treatment with soil incorporation. The chemicals were incorporated by mixing them into the top two inches (5 cm.) of soil prior to planting the seeds. The plants were evaluated 28 days after treatment and the results are given in Table IV.

TABLE IV

| Plant | Compound 1 | | Compound 2 | | Compound 8 | |
|---|---|---|---|---|---|---|
| Species | 0.5 lb. | 1 lb. | 0.5 lb. | 1 lb. | 0.5 lb. | 1 lb. |
| pigweed | 0 | 9 | 8/2 | 9 | 9 | 9 |
| peanuts | 0 | 0 | 0 | 0 | 0 | 0 |
| sesbania | 5/1 | 5/3 | 9 | 9 | 8/3 | 9 |
| prickly sida | 6/1 | 8/3 | 8/3 | 8/4 | 7/2 | 9 |
| foxtail | 0/2 | 0/3 | 0/1 | 8/4 | 5/2 | 6/3 |
| jimsonweed | 6/1 | 8/3 | 8/2 | 9 | 8/4 | 8/4 |
| velvetleaf | 0 | 6/2 | 9 | 9 | 0/1 | 7/3 |
| morning-glory | 0/1 | 7/2 | 6/2 | 9 | 0/2 | 9 |
| wild oats | 0 | 0/1 | 6/2 | 8/3 | 0/1 | 8/3 |
| cocklebur | 0/1 | 5/2 | 0/2 | 8/2 | 0/1 | 6/4 |
| Johnson-grass | 0/1 | 0/2 | 0/1 | 0/2 | 0/1 | 0/2 |
| barnyard-grass | 0/2 | 5/3 | 5/2 | 5/2 | 0/2 | 5/3 |
| soybeans | 0/1 | 0/2 | 0/1 | 0/2 | 0/1 | 0/2 |
| corn | 0 | 0/1 | 0 | 0/2 | 0/1 | 0/2 |
| field beans | 0/2 | 6/3 | 0/1 | 0/1 | 0/1 | 9 |
| cotton | 0 | 0/1 | 0/2 | 8/4 | 0 | 5/2 |
| rice | 5/1 | 5/2 | 5/2 | 9 | 5/2 | 6/3 |
| sorghum | 0/2 | 0/3 | — | — | 0/1 | 0/3 |
| ragweed | 9 | 9 | 9 | 9 | 5/2 | 9 |
| lambs-quarters | — | — | 9 | 9 | 9 | 9 |
| mustard | — | — | 8/2 | 9 | 8/3 | 9 |
| nightshade | — | — | 9 | 9 | 8/2 | 7/4 |

Since a relatively small amount of one or more of the active compounds should be uniformly distributed over the area to be treated, they preferably are formulated with conventional herbicide carriers, either liquid or solid. Thus, the compounds can be impregnated on or admixed with a pulverulent solid carrier such as lime, talc, clay, Bentonite, calcium chloride, vermiculite and the like. Alternatively, they can be dissolved or suspended in a liquid carrier such as water, kerosene, alcohols, diesel oil, mineral oil, xylene, benzene, glycols, ketones, and the like. Since the compounds will form water-soluble salts such as with mineral acids, they can be readily formulated with water.

A surfactant is preferably included to aid in dispersion, emulsification and coverage. The surfactant can be ionic or non-ionic and may be liquid or solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium salts of petroleum-derived alkylsulfonic acids, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 95 percent by weight of one or more of the active compounds with a carrier or diluent, which may be a liquid or a solid. Liquid carriers which are miscible with the active agent or other liquids in which the compound may be suspended or dispersed, can be used. A surfactant is also generally included to facilitate such dilution or dispersion in water. However, the surfactant itself may comprise the carrier in such concentrates.

Various changes and modifications of the invention can be made, and, to the extent that such variations incorporate the spirit of this invention, they are intended to be included within the scope of the appended claims.

What is claimed is:

1. The method for controlling weed growth which comprises applying to the locus of said weeds a phytotoxic amount of a compound of the formula

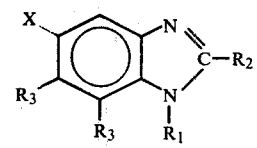

in which each of $R_1$ and $R_2$ are lower alkyl of one to about three carbon atoms, X represents a lower alkylsulfonyl or fluoro-lower alkylsulfonyl group and each of said $R_3$'s is selected from hydrogen, halo, lower alkoxy, nitro and amino groups.

2. The method according to claim 1 in which both $R_3$'s are hydrogen.

3. The method according to claim 1 in which X is a fluoro-lower alkylsulfonyl group.

4. The method according to claim 1 in which said compound is applied at a rate of 0.5 to 5 pounds per acre.

5. The method according to claim 1 in which said compound is applied to the foliage of said weeds.

6. The method according to claim 1 in which said compound is applied to the soil and incorporated within the top 3 inches of soil.

7. The method according to claim 2 in which said X is difluoromethylsulfonyl.

8. The method according to claim 2 in which said X is trifluoromethylsulfonyl.

9. A method according to claim 2 in which said X is methylsulfonyl.

10. The method according to claim 2 in which said compound is 1-ethyl-2-methyl-5-difluoromethylsulfonylbenzimidazole.

11. The method according to claim 2 in which said compound is 1,2-dimethyl-5-difluoromethylsulfonylbenzimidazole.

12. The method according to claim 2 in which said compound is 1-ethyl-2-methyl-5-trifluoromethylsulfonylbenzimidazole.

13. The method according to claim 2 in which said compound is 1,2-dimethyl-5-methylsulfonylbenzimidazole.

* * * * *

UNITED STATES PATENT OFFICE
CERTIFICATE OF CORRECTION

Patent No. 4,177,057          Dated Dec. 4, 1979

Inventor(s) DON L. HUNTER and WAYNE S. BELLES

It is certified that error appears in the above-identified patent and that said Letters Patent are hereby corrected as shown below:

In Column 2, Line 25, delete $\left[\xrightarrow[H_2SO_4]{NHO_3}\right]$ and add --- $\xrightarrow[H_2SO_4]{HNO_3}$ --- .

Signed and Sealed this

Twelfth Day of February 1980

[SEAL]

Attest:

SIDNEY A. DIAMOND

Attesting Officer     Commissioner of Patents and Trademarks